United States Patent [19]
Morein

[11] Patent Number: 5,254,339
[45] Date of Patent: Oct. 19, 1993

[54] PROCESS FOR PREPARING IMMUNE COMPLEXES

[76] Inventor: Bror Morein, Ollonstigen 3, Vreta, S-75590 Uppsala, Sweden

[21] Appl. No.: 70,920
[22] PCT Filed: Oct. 16, 1986
[86] PCT No.: PCT/SE87/00480
  § 371 Date: Jun. 1, 1987
  § 102(e) Date: Jun. 1, 1987
[87] PCT Pub. No.: WO87/02250
  PCT Pub. Date: Apr. 23, 1987

[30] Foreign Application Priority Data
  Oct. 16, 1985 [EP] European Pat. Off. ........ 85850326.1

[51] Int. Cl.$^5$ ...................... A61K 39/00; A61K 39/39
[52] U.S. Cl. ...................... 424/88; 424/89; 424/90; 424/91; 424/92; 514/2; 514/8
[58] Field of Search .............. 424/88, 89, 90, 91, 424/92, 450; 530/806, 403

[56] References Cited

U.S. PATENT DOCUMENTS

| | | | |
|---|---|---|---|
| 4,053,585 | 10/1977 | Allison et al. | 424/92 |
| 4,157,390 | 6/1979 | Parry et al. | |
| 4,196,191 | 4/1980 | Almeida et al. | |
| 4,201,767 | 5/1980 | Fullerton et al. | |
| 4,356,169 | 10/1982 | Simons et al. | |
| 4,459,286 | 7/1984 | Hilleman et al. | |
| 4,578,269 | 3/1986 | Morein | 424/88 |
| 4,806,350 | 2/1989 | Gerber et al. | 424/88 |
| 4,900,549 | 2/1990 | DeVries et al. | 424/88 |

FOREIGN PATENT DOCUMENTS

| | | |
|---|---|---|
| 0037931 | 10/1981 | European Pat. Off. |
| 0047480 | 3/1982 | European Pat. Off. |
| 0109942 | 5/1984 | European Pat. Off. |
| 0117783 | 9/1984 | European Pat. Off. |
| 0142192 | 5/1985 | European Pat. Off. |
| 0142193 | 5/1985 | European Pat. Off. |
| 231039 | 8/1987 | European Pat. Off. |
| 2104527 | 3/1983 | United Kingdom |
| WO83/02069 | 6/1983 | World Int. Prop. O. |
| WO84/03506 | 9/1984 | World Int. Prop. O. |

OTHER PUBLICATIONS

"Protein Micelles and Virosomes From the Surface Glycoproteins of Parainfluenza 3 Virus", *Chemical Abstracts*, vol. 96, No. 21, May 24, 1982, Abstract No. 176474d, By B. Morein et al., p. 285.

"Iscom, A Novel Structure for Antigenic Presentation of Membrane Proteins From Enveloped Viruses", *Nature*, vol. 308, No. 29, Mar. 1984, By B. Morein et al., pp. 457–459.

*Primary Examiner*—Sam Rosen
*Attorney, Agent, or Firm*—Young & Thompson

[57] ABSTRACT

A process is provided for preparing an immunogenic complex containing antigenic proteins and peptides with hydrophobic domains, whereby proteins or peptides from viruses, mycoplasmas, bacteria, parasites, animal cells with hydrophobic domains are mixed with one or more solubilizing agents, whereby complexes are formed between proteins or peptides and the solubilizing agent, where after the proteins or peptides are separated from solubilizing agent in the presence of, or are separated from, the solubilizing agent and directly transferred to a glycoside solution, containing one or more glycosides with hydrophobic and hydrophilic domains in a concentration of at least the critical micellar concentration, thereby forming a protein complex which is isolated and purified, characterized in that lipids are added before the complex is isolated and purified.

19 Claims, 1 Drawing Sheet

PROCESS FOR PREPARING IMMUNE COMPLEXES

Figure 1:
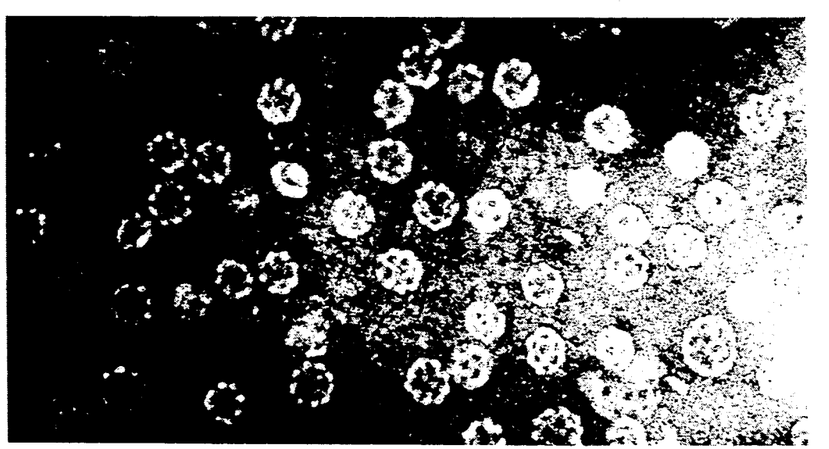

This invention relates to a new process for preparing an immunogenic complex so-called iscom.

It is known that killed viruses for example influenza virus, have a good antigenic effect. They are, however, pyrogenic even after extensive purification. By isolation of components which are important for induction of protective immunity, the pyrogenic effect has been avoided, but the immunogenicity is often not sufficiently strong. Therefore suitable adjuvants must be introduced in those vaccines containing the isolated antigens (subunits) in order to increase the immune response. On the other hand, effective adjuvants cause, in the manner in which they have been used up to now, negative side effects. Adjuvantcontaining vaccines are thus no better than vaccines based on the entire virus, as regards the pyrogenic effect.

In order to increase the immunogenicity, detergent membrane proteins have been produced, which have been entrapped or bound to the surface of liposomes (EPC Application 7940083.0). Detergent-free membrane proteins in liposomes are described in U.S. Pat. No. 4,148,876. Incorporation of adjuvants in such detergent-free unilamellar liposome products is mentioned in U.S. Pat. No. 4,196,191 (without reporting on the effect thereof). U.S. Pat. No. 4,117,113 describes negatively charged liposomes containing virus antigen. In such liposomes containing influenza haemaglutinin and neuraminidase, incorporation in liposomes of an adjuvant, mycobacterial cell walls, produces a better immune response. Better immune responses have also been obtained when adjuvants such as killed Mycobacterium tuberculosis, Bordetella pertussis and saponins have been introduced in such negatively charged liposomes containing diphtheria toxoid (U.S. Pat. No. 4,053,585). All of the above-mentioned lipid-containing membrane protein products are, however, unstable after long storage, freeze-drying or uncareful handling, e.g. high temperature.

Detergent-free and lipid-free protein micelles have also been produced as vaccine. It has been demonstrated that micelles of membrane proteins of Semliki Forest Virus (SFV) stimulate the formation of circulating antibodies against SFC and produce a protection in mice against fatal infection by SFV. On the other hand, such membrane protein micelles of parainfluenza-3-virus were not effective for stimulating antibody formation in lambs or protecting them against a dose of a PI-3-virus causing pneumonia, unless an oil adjuvant was mixed with the micelles. Oil adjuvants usually produce side effects in the form of local reactions at the infection site (EPC Application 81102213-6).

In EPC-patent application 0 109 942 there is described an immunogenic protein or peptide complex containing glycosides and a process for preparing the same. According to the process one can start from whole viruses, mycoplasmas, bacterias, parasites, animal cells but also from purified peptides or proteins or from proteins or peptides synthesized or produced by hybrid DNA technique.

These complexes have another morphological structure under electron microscopy than corresponding protein micelles produced without the addition of glycosides. The micelles have a compact central core with radially arranged spikes, while the complex according to EPC 0 109 942 has an open spherical structure consisting of circular subunits or parts of the spheric structure. The morphology is also different from that of liposomes. The complexes and the parts thereof also usually have a lower sedimentation constant than corresponding micelles and a higher sedimentation constant than the corresponding monomeric form of protein or peptide, and higher sedimentation constant than liposomes.

The complexes according to EPC 0 109 942 which have been produced with the addition of glycosides, have better immunogenic activity than corresponding protein micelles produced without the addition of glycoside or complex between a protein molecule and solubilizing agent (monomeric forms) or protein molecules bound to lipid vesicles, i.e. virosomes and produce fewer side effects than when the protein micelles are mixed with the glycosides or other adjuvants. Thus the dose of membrane proteins can be reduced to about 1/10 or more.

It has now turned out that when starting from pure proteins or peptides they tend to form aggregates, i.e. micelles. This can be overcome by adding lipids when preparing the complex.

Also when starting from bacterias and when whole cells are purified there might be too little of lipids present so that micelles are formed. This can be overcome by the addition of lipids.

It has also turned out that the new method can be used for preparing complexes with antigens other than peptides or proteins and with antigenic determinants.

Thus, the present invention concerns a process for preparing immunogenic complex containing antigens or antigenic determinants with hydrophobic domains, whereby viruses mycoplasmas, parasites, animal cells, antigens or antigenic determinants with hydrophobic domains are mixed with one or more solubilizing agents whereby complexes are formed between antigens or antigenic determinants and solubilizing agent, where after the antigens or antigenic determinants are separated from solubilizing agent in the presence of, or separated from the solubilizing agent and directly transferred to a glycoside solution, containing one or more glycosides with hydrophobic and hydrophilic regions in a concentration of at least the critical micellular concentration, thereby forming a protein complex which is isolated and purified, characterized in that lipids are added before the complex is isolated and purified.

To enhance the solubilization and maintain the amphiphatic proteins or proteins with hydrophobic domains naturally exposed or exposed by chemical treatment or heat (e.g. 70° C.) or other molecules with hydrophobic domains, dispergate as monomers in an aqueous solution the presence of lipids and/or polar organic solvents miscible in water might be essential. In effect in nature lipids are used for that purpose both in animal and plant cells. Therefore, any lipid-lipid mixture found in membranes from animal cells or from plant cells will be suitable. Some lipids make lipid membranes more rigid, e.g. cholesterol, others more fluid, e.g. phosphatidylcholine. Synthetic lipids can also be produced, which have these required properties and there are virtually no restrictions to formulate new lipids which may be used for these purposes.

As regards the size of and properties of the lipid, the limitations are determined by the solubility in the system used. E.g. aqueous solutions of rigid lipids (cholesterol) is stabilized by addition of less rigid lipids (phosphatidylcholine). Polar organic solvents participate in the stabilization of the protein with hydrophobic properties in solution as a protein monomer. In conclusion it is not possible to limit the size of the lipid as regards its function because, e.g. the length of an aliphatic chain determining the hydrophobic properties can be counterbalanced by a matching polar moiety.

Also sugars have a stabilizing effect to maintain proteins with exposed hydrophobic regions or other molecules with similar properties dispergate as monomers in solution. As sugars there can be used monosaccharides such as trioses, tetroses, pentoses, hexoses, heptoses and the corresponding ketoses, not reducing aligosaccharides such as sucrose, trehalose, raffinose, reducing oligosaccharides such as maltose, cellobiose, isomaltose, panose, gentiobiose, lactose and polysaccharides. They can be added in an amount of 5-50% of the water solution.

As polar organic solvents miscible in water there can be used alcohols such as mono- or polyhydric alcohols with up to 10 carbon atoms such as ethanol, glycols such as ethylene glycol, ethers such as diethylether, ketones, such as acetone.

The lipids can be fats or fat resembling substances such as triglycerides or mixed triglycerides containing fatty acids with up to 50 carbon acids such as saturated fatty acids with 4-30 carbon atoms e.g. butyric acid, caproic acid, caprylic acid, capric acid, lauric acid, myristic acid, palmitic acid, stearic acid, arachidic acid, behenic acid, lignoceric acid, or unsaturated fatty acids with up to 30 carbon atoms, such as hexadecene acid, oleic acid, linoleic acid, linolenic acid, arachidonic acid; hydroxy-fatty acids such as 9,10-dihydroxy stearic acid, unsaturated hydroxy fatty acids such as castor oil, branched fatty acids; glycerol ethers, waxes i.e. esters between higher fatty acids and monohydric alcohols; phospholipides such as derivatives of glycerol phosphates such as derivatives of phosphatidic acids i.e. lecithin, cephalin, inositol phosphatides, spingosine derivatives with 14-20 carbon atoms; glycolipids isoprenoids, sulpholipids, carotenoids, steroids, such as cholesterol, cholestanol, caprostanol, phytosterols, e.g. stigmasteroll sitosterol, mycosterols, e.g. ergosterol, bile acids e.g. cholic acid, deoxycholic acid, chenodeoxycholic acid, litochclic acid, steroid glycosides, esters of vitamine A, or mixtures thereof.

These and other useful lipids are described in: Lipid biochemistry an introduction, Ed. M.I. Gurr, A.I. James, 1980 Chapman and Hall, London, New York, University Press Cambridge, which hereby is incorporated as a reference.

Preferably cholesterol phosphatidylcholine, liposomes or intralipid ® (Oleum soya fractionate 200 g, Lechitinum fractionate vitello ovi 12 g, glycerol 22.5 g H $_2$O ad 1 l) are used.

The lipids can be added at any stage in the process, preferably before the addition of the glycoside but lipids could also be added after the glycoside. If lipids are not present the antigens or antigenic determinants tend to form micelles. The addition of lipids breaks up the micelles so that the complex can be formed.

The lipids are added in a molar ratio of at least 0.1/1 of lipids to antigens or antigenic determinants preferably at least 1/1.

If more tharl a molar ratio of 100/1 is used the complex becomes sticky and difficult to handle. If less is used micelles might occur and less complex is formed. At a ratio of 0.1/1, however, there is still formed some complex. The molar ratio of lipids to antigens or antigenic determinants is thus from 0.1/1 to 100/1.

It cannot be proved by analytical methods available today if the lipids are incorporated or not. The complexes produced with lipid addition according to the new method have the same morphological structure under electron microscopy (EM) (see FIG.) and the same sedimentation constant as complexes produced without the additive of lipids (see above).

If, however, the complexes produced by lipid addition are not cleaned afterwards, their outlines in EM are hazy and it is believed that lipids are aggregated on their surfaces. When the complexes are cleaned their outlines in EM are quite clear and one cannot at present prove that they contain lipids.

As antigens can be used macromolecular compounds. Besides proteins, polypeptides, glycoproteins, and lipoproteins there can also be used polysaccharides, oligosaccharides, polynucleotides or mixtures thereof.

Antigenic determinants suitable ilor preparing complexes according to the invented process are for example small polypeptides, small oligosaccharides, oligonucleotides, glycoprotein fragments and haptenes or mixtures thereof.

With small polypeptides are meant here polypeptides comprising at least 3 up to about 40 amincacids. In general an antigenic determinant comprises not more than 4-10 amino acids. Sometimes, however, a somewhat larger number of amino acids is needed in order to ensure the specific structure of the antigenic determinant and/or immune response upon immunisation.

With small oligosaccharides are meant linear or branched chains of sugar units comprising at least 4 and up to about 20 sugar units, preferably between 6 and 10 sugar units. These oligosaccharides can be prepared synthetically or by chemical or enzymic degradation of naturally occurring polysaccharides or glycoproteins.

With cligonucleotides are meant compounds consisting of at least 1 up to about 18 deoxyri-bonucleotides or ribonucleotides which are obtained synthetically, or by enzymatic or chemical cleavable of polynucleotides such as RNA and DNA. Optionally these oligonucleotides may be doublestranded.

By haptenes are meant small molecules which are not immunogenic by themselves but bound to a carrier molecule they become immunogenic. Examples are steroids and prostaglandins.

The antigens or antigenic determinants are to possess hydrophobic groups or at least one reactive group which can form a bond between the antigen or antigenic determinant and hydrophobic compounds, e.g. those mentioned on page 23, 3rd paragraph to page 25, 1st paragraph.

Molecules not immunogenic by themselves can if they have hydrophobic groups be complex into iscoms together with bigger groups which are immunogenic and which play the role of carriers in the iscom complex. Thus the complex can contain mixtures of haptenes and antigens.

The proteins or peptides with hydrophobic domains that are bound to hydrophobic regions of the glycosides may be A) amphiphatic proteins or peptides with hydrophilic and hydrophobic groups derived from or being membrane proteins or membrane peptides from enveloped viruses, bacteria, mycoplasmas, parasites or animal cells, or such proteins or peptides produced by hybrid DNA technique, or molecules produced synthetically.

B) hydropholic proteins or peptides made amphiphatic by hydrophobic groups being coupled to them. These proteins or peptides may derive from viruses, bacteria, mycoplasmas, parasites, whole cells or be synthesized or obtained by hybrid DNA technique.

C) amphiphatic proteins or peptides obtained by inaccessible hydrophobic parts of hydrophilic proteins being made accessible by chemical means or by high temperature. These proteins may derive from the microorganisms or cells mentioned above or obtained by hybrid DNA technique, or be synthesized.

Preparation of complex a) Concerning the preparation of membrane proteins or membrane peptides derived from whole cells or viruses, the preparation of the complexes comprises in principle three steps: purification or isolation of animal cells or microorganisms or fragments thereof; solubilizing of hydrophobic proteins and removal of the solubilizing agent while at the same time transferring the desired antigen in complex by means of glycoside in an immunogenic form (immunogenic complex).

Purification and isolation

Viruses, mycoplasmas bacteria, carasites and animal cells are concentrated and purified in a known manner (for references see "The Tools of Biochemistry", T G Cooper, John Wiley & Sons (1977) New York, which is incorporated as a reference) for example by gel filtration or centrifuging through a sugar gradient or gradient centrifuging through percoli or-with hollow fiber dialysis. For bacteria, it can be necessary or more advantageous to first lyse or break down the cell walls (for references see Cota-Robles and Stein, CRC Handbook of Microbiology Vol II (1973) pp 833–844 which is incorporated as a reference) with ultrasond or French press treatment for example. It might be useful to add lipids if the cells are strongly purified.

Solubilizing

The purified animal cells or microorganisms or fragments thereof are then mixed with non-ionic, ionic or Zwitterionic detergent or detergent based on gallic acid which is used in excess. Typical examples of suitable non-ionic detergents are polyglycol esters and polyglycol ethers with aliphatic or arylaliphatic acids and alcohols. Examples of these are alkylpolyoxyethylene ethers with the general formula $F_nH_{2n+1}(OCH_2CH_2)_xOH$, shortened to $C_nE_x$; alkylphenyl polyoxyethylene ethers containing a phenyl ring between the alkyl group and the polyoxyethylene chain, abbreviated $C_nE_x$, e.g. Triton X-100=tert. - $C_8E_{9,6}$ (octyl-phenolether of polyethylene oxide), N-alkanoyl ($C_1$–$C_{30}$)-N-methylglucamin e.g. N-dekanoyl or nonanoyl-N-methylglucamin acylpolyoxyethylene esters: acylpolyoxyethylene sorbitane esters, abbreviated $C_n$ sorbitane $E_x$, e.g. Tween 20, Tween 80, -D-alkyln glucosides, e.g. -D-octylglucoside. The glycosides mentioned below can also be used, especially saponin. These are, however, weak detergents and should be used together with other detergents. Typical examples of suitable ionic detergents are gallic acid detergents such as e.g. desoxycholate and cholate. Even conjugated detergents such as e.g. taurodeoxycholate, glycodeoxycholate and glycocholate can be used. Possible Zwitter-ionic detergents are lysolecitin and synthetic lysophospholipids. Even mixtures of the above-mentioned detergents can be used.

Solubilizing can also be performed with alcohols, organic solvents or small amphiphatic molecules such as heptane-1,2,3-triol, hexane-1,2,3-triol, acetic acid, or mixtures thereof, or with detergents.

The solubilizing agent is used in excess in relation to the amount of lipid and hydrophobic proteins. Suitably cells or microorganisms and detergents are mixed in the weight ratio 1:3 to 1:10.

Cells or microorganisms and solubilizing agent are mixed in buffered possibly saline solution. The molarity of the saline solution lies between 0.02 and 0.5 M, preferably between 0.05 and 0.25 M, 0.1–0.2 M is preferred. The detergent should act for about 1 hour at room temperature. Sodium chloride is preferred as a salt, but other salts can also be considered, especially salts with alkali ions, earth alkali ions and ammonium ions and strong mineral acids and organic acids such as acetic acid, trichloroacidic acid, formic acid and oxalic acid. As a buffer, all substances are suitable which buffer in the pH interval 6.5-9. When using cholates and desoxycholates, pH 8-9 is preferred, and when using non-ionic detergents, pH 7.4. When organic acids are used for protein solubilization, buffering may be omitted.

The preparation of immunogenic complexes

When cells or microorganisms have been solubilized, a mixture of solubilizing agent and cell or microorganism fragments are formed (hereinafter called fragments). Among the fragments there are charged monomeric antigenic proteins with hydrophobic regions in complex with the solubilizing agent. The new immunogenic complex according to the invention is produced by separating the charged monomeric antigenic proteins from the solubilizing agent in the presence of, or by directly transferring to, one or more glycosides which must have hydrophobic and hydrophilic regions and be present in a concentration of at least the critical micelle concentration. The rest of the fragments are removed before the complex according to the invention is produced, while it is being produced, or afterwards, preferably before.

The complex according to the invention can be produced either by removing the solubilizing agent, e.g. by dialysis, gel- filtration or chromatography from the mixture of solubilizing agent, charged monomeric antigenic proteins, glycoside and possibly other fragments or by separating the charged, monomeric, antigenic proteins from said mixture, e.g. by gradient centrifuging, chromatography or electrophoresis. The essential feature of the invention is that the monomeric antigenic proteins are separated from the solubilizing agent during the simultaneous presence of the glycoside or after separation are directly transferred to the glycoside, of which the micelle form should be present. When the monomeric antigenic proteins are separated from the solubilizing agent so that they can come directly into contact with the glycoside, the special complex according to the invention is formed. It is assumed that the micelle form of the glycoside is the base for forming the complex and that this is formed by attraction between hydrophobic regions on the glycoside micelles and hydrophobic regions on the membrane proteins. The amount of glycoside in the complex varies depending on the glycoside used and the complex bound membrane proteins and lies between 0.5 and 50% by weight, especially between 0.5 and 25% by weight, preferably between 0.5 and 15, often between 0.5 and 10% by weight, and especially between 2 and 8% by weight. If the charged antigenic monomeric proteins are separated from the solubilizing agent in the absence of the glycoside, protein micelles of the type produced according to EPC Application 81102213.6 are formed however.

It is suitable to remove the other fragments by gradient centrifuging since the sedimentation constant for the components involved decreases in the following order: cell fragment, protein complex with solubilizing agent or according to the invention, monomeric proteins and solubilizing agent. Thus, the other fragments can be removed with gradient centrifuging from the mixture of solubilizing agent, monomeric proteins, and other fragments before the glycoside is added and the solubilizing agent removed, e.g. by dialysis, gel filtration, chromatography or the monomeric proteins are separated from the solubilizing agent, e.g. by electrophoresis, chromatography or gradient centrifuging. In the latter method, it is also possible to remove the other fragments during the same gradient centrifuging, as the complex is formed. It is also possible to separate other cell components after the complex has been formed according to the above, e.g. by centrifuging, affinity chromatography, gel filtration. Materials not integrated into iscoms but bound to them by hydrophobic interaction can be removed by centrifugation through a zone of detergent e.g. a gradient of sugar or a sugar solution containing detergent.

The glycoside can be any glycoside at all with hydrophobic and hydrophilic regions. Preferably, the saponins are used which are described in R Tschesche and Wulf, Chemie und Biologie der Saponine in Fortschritte der Chemie Organischer Naturstoffe, published by W Herz, H Grisebach, G W Kirby, Vol 30 (1973), especially the strongly polar saponins, primarily the polar triterpensaponins such as the polar acidic bisdesmosides, e.g. saponin extract from Quillajabark Araloside A, Chikosetsusaponin IV; CalendulaGlycoside C, Chikusetsusaponin V, Achyranthes-Saponin B, Calendula-Glycoside A, Araloside B, Araloside C, Putraniia-Saponin III, Bersamasaponoside, Putranjia-Saponin IV, Trichoside A, Trichoside B, Saponaside A, Trichoside C, Gypsoside, Niitanoside, Dianthoside C, Saponaside D, preferablyi aescine from Aesculus hippocastanum (T Patt and W Winkler: Das therapeutisch wirksame Prinzip der Rosskastanie (*Aesculus hippocastanum*), Arzneimittelforschung 10 (4), 273-275 (1960) or sapoalbin from *Gypsophilla struthium* (R Vochten, P Joos and R Ruyssen: Physics-chemical properties of sapoalbin and their relation to the foam stability, J Pharm Belg 42, 213-226 (1968), especially saponin extract from *Quillaja saponaria Molina*, primarily the DQ-Extract which is produced according to K Dalsgaard: Saponin Adjuvants, Bull Off Irit Epiz 77 (7-8), 1289-1295 (1972) and Quil A which is produced according to K Dalsgaard: Saponin Adjuvants III, Archiv für die Gesamte Virusforschung 44, 243-254 (1974). Also mixtures of glycosides can be used. The amount of glycoside added should be at least 1-3 times their critical micelle formation concentration (CMC), preferably at least 5, especially at least 7-12 times. It is assumed that the glycoside in this case can be bound to and catch monomer forms of the membrane proteins. Preferably Quil A is used, which has a critical micelle formation concentration of 0.03% by weight. The amount of Quil A should then be at least 0.02% by weight, especially 0.05-0-5% by weight, preferably 0.2% by weight. The citations above concerning the glycosides are incorporated as references.

The separation of the charged monomeric antigenic proteins from the solubilizing agent has been done by centrifugation, dialysis, electrophoresis, and different chromatographic methods.

The centrifuge method

The mixture of fragmented cells or microorganisms and solubilizing agent made according to the above is gradient-centrifuged and layered on top of e.g. a sugar or salt solution, containing solubilizing agent, under which a gradient containing the glycoside is present, such as a sugar gradient or a gradient of glycerol or metrize amide or a heavy salt, e.g. CsCl (i.e. relative inert substances which have suitable density, viscosity to act as gradient material), e.g. with the concentrations for a sugar gradient given below.

The gradient system is centrifuged at at least 100,000 g. As sugar there can be used monosaccharides such as lactose, maltose, disaccharides such as lactose, maltose, saccharose, but also trioses, tetroses and glycerine. Preferably saccharose is used. The sugar concentration in the gradient is suitably at least 5, preferably 15-25% by weight as beginning concentration (uppermost in the gradient) and the final concentration is at least 20, preferably 45-60% by weight (lowermost in the gradient). The gradient can for example consist of an upper layer with 5-25% by weight sugar content and a lower layer with 20-60% by weight sugar content. However, there can also be several layers, the concentration differences between the individual layers being reduced correspondingly. The sugar gradient contains a glycoside or a mixture of glycosides. The amount of glycoside should be at least 1-3, preferably at least 7-12 times CXC for Quil A at least 0.02, especially at least 0.05-0.5, preferably at least 0.2% by weight. In this glycoside containing gradient the solubilizing agent is separated, and the complex between the solubilizing agent and the protein is transformed to protein-glycoside complex.

On top of the sugar gradient there is a layer of a solution of sugar or heavy salt which contains solubilizing agent or a mixture of solubilizing agents. The lipids are remaining in this layer. The concentration of solubilizing agent in this layer is less than or the same as in the applied mixture of microorganisms or cells and solubilizing agent and lies suitably between 0.12 and 3% by weight, preferably between 0.75 and 1.5% by weight, with 1% by weight being preferred. The sugar or salt concentration can be the same a3 or less than the concentration in the upper layer of the gradient, preferably 5-25% by weight especially 15% by weight.

After centrifugation at at least 100,000 g for at least 16 h, preferably for 20 h at 200° C., the proteinaceous fractions are collected and dialyzed against buffer (0.5 M to 0.001 M) preferably 0.005 M Tris-HCl, 0-01 M NaCl, pH 7.4 or 0.2 M ammonium acetate buffer, pH 7.0 and is concentrated e.g. as described in The Tools of Biochemistry by T G Cooper, edit John Wiley & Sons (New York 1974) which is incorporated as a reference, e.g. by lyophilisation, vacuum dialysis and ultra filtrating. During the centrifugation, all constituents are settling whereby the solubilizing agent loosens from the complex of protein and solubilizing agent, and the monomeric proteins are transferred to the glycoside and form complexes therewith. In the subsequent dialysis the sugar is taken away.

The complex can possibly be purified further, e.g. from free glycoside by gradient centrifuging, e.g. by a sugar gradient containing 25-60% by weight sugar, preferably 10-40% by weight saccharose. If the top of the gradient contains detergent, the free glycoside is even more trapped.

The dialysis method

After purification of cells or the microorganisms as described above and after they have been mixed with solubilizing agent in the above described weight ratio, the mixture of cells and solubilizing agent, in the above described buffer can alternatively directly be mixed with at least 1-3, preferably 7-12 times CMC for Quil A 0.05-2% by weight glycoside, preferably 0.1-0.2% by weight glycoside and be dialyzed against the buffer such as 0.5-0.001 M, preferably 0.005 M Tris-HCl, 0.01 M NaCl, pH 7.4, especially 0.2 M ammonium acetate buffer, pH 7.0. The mixture of solubilizing agent and cells may include lipids and ethanol particularly useful for immunogenic proteins purified by affinity chromatographic methods or peptides, synthetically produced. The dialysis separates the solubilizing agent in the presence of the glycoside. The membrane protein complex produced can then be isolated with sedimentation gradient centrifuging, such as is described on page 9, last paragraph, the glycoside additive is excluded, however, and is freed from the other fragments and free glycoside.

The mixture of cells and microorganisms and solubilizing agent in buffer can also be gradient centrifuged and e.g. be layered on a 5-60% by weight sugar gradient in the above buffer, preferably a 10-20% by weight saccharose gradient and be centrifuged at at least 150,000 g for at least 20 minutes, preferably for 30 minutes at 250,000 g. The other fragments are thereby separated from the Complex between solubilizing agent and protein.

The proteinaceous upper liquid, called top fraction, is extracted and the glycoside is added in an amount of at least 1-3, preferably at least 7-12 times CMC for Quil A 0.05-0.5% by weight, preferably 0.2% by weight, and is dialyzed against buffer 0.50-001 M, especially 0.005 M Tris-HCl, 0.01 M HCl, pH 7.4, preferably 0.2 M ammonium acetate. The solubilizing agent is removed in the presence of the glycoside. Further purification can be done with sedimentation gradient centrifuging (see page 16, second paragraph). Further purification can be done by centrifugation through a sugar gradient containing 5-60% by weight sugar, preferably 10-40% by weight sugar, eventually containing a top layer of sugar with detergent.

The electrophoresis method

Alternatively, the mixture of fragmented microorganisms or cells and solubilizing agent or the proteinaceous top liquid (other fragments and free solubilizing agent removed) which is obtained, when the mixture is gradient-centrifuged e.g. by a 5-60% by weight, preferably 10-20% by weight sugar gradient in buffer, is separated by electrophoresis from the solubilizing agent and is transferred in a solution containing at least 1-3, preferably at least 7-12 times CMC, for Quil A 0.05-0.51 by weight glycosides, preferably 0.2% by weight glycoside. The charged monomeric antigenic proteins are thereby separated from the solubilizing agent. For separation by electrophoresis, it is suitable that the solubilizing agent-buffer solution not contain extra added salt which can interfere with the electrophoresis and produce excessively high temperature. It is possible to use e.g. zone electrophoresis with or without carriers and isotakophoresis with or without carriers. Common substances can be used as carriers such as polyacrylamide, agar, silica gel, starch, cellulose, polyvinylchloride, ion exchanger, celite. Isolation and concentration of complexes are done as described on page 10, lines 23-26.

Further purification with gradient-centrifuging (see page 16, second paragraph).

If hydrophobic membrane proteins with various charges or weight are present in the starting material, it is possible with electrophoresis or the centrifuging methods to separate them from each other and produce separate complexes of them. With these conditions, all is possible to separate and enrich complexes of various membrane proteins.

Chromatographic methods

The solubilized proteins can optionally, after being purified from cell fragments, be separated from the solubilizing agent with chromatographic methods, e.g. gel filtration or the antigen structure being adsorbed into an insoluble substratum (matrix) which may consist of e.g. cellulose, agarose, dextrane, acrylamide, and glass. Different liganus are coupled to the matrix structure which then receives specific properties which are utilized during the separation. The antigen structure is usually adsorbed at the same time as the solubilizing agent used passes unadsorbed through the matrix. Then follows desadsorbation of the antigen. During the desadsorbation step there can take place an exchange of solubilizing agent, salt and buffer substance, the solubilizing agent being replaceable by the glycoside, and complex being formed. The solubilizing agent can be supplemented with lipid and alcohol which enhances the formation of iscoms.

In ion exchange chromatography, charged ligand molecules such as diethylaminoethyl (DEAE) are coupled to matrix and employed as cation exchangers. Carboxyl methyl (CM) or phosphate groups (P) are coupled to matrix and employed as anion exchangers. By using differences in net charge between antigen structures and solubilizing agent, these molecules are separated. In general the solubilizing agent is uncharged and the protein charged. Elution is performed with salt gradient such as K or NaCl or pH adjustment with phosphate buffer in the presence of a solubilizing agent (as to concentration and example see section Solubilizing above). The solubilizing agent can be supplemented with lipid and alcohol which enhances the formation of iscoms. At elution the protein can be purified, the solubilizing agent exchanged or the complex formed if the glycoside is added to the eluant instead of solubilizing agent. Salts are subsequently removed by dialysis.

In gel filtration it is made use of the solubilizing agent being smaller than the antigen structures and coming out in subsequent fractions.

By means of immunoaffinity-chromatography antibodies can be irreversibly bonded to the matrix mentioned above, where after the unique specificity and affinity of antibodies are utilized for purifying the desired antigen structure. The solubilizing agent has no affinity for antibodies. Elution is performed by mild denaturation, e.g. pH reduction to about 4 and in the presence of solubilizing agent or glycoside.

In lectin chromatography lectins are used, a group of proteins capable of reacting reversibly with specific sugar groups, which makes it possible for them to bind glycoproteins, for example. The lectin is coupled as ligand to e.g. Sepharose (Pharmacia, Uppsala) or is commercially bought ready-coupled to a suitable matrix. Detergents (solubilizing agents) have no affinity for the immobilized lectin. The adsorbed antigen structure is usually desadsorbed by addition of methylated sugar such as methyl mannoside, methyl glucoside and N-acetylglycosamine dissolved in buffered salt solution in the presence of solubilizing agent or glycoside.

In covalent chromatography, an antigen structure with a thiol group with a covalent bond is bonded to matrix. The thiol group in the antigen is selectively bonded to an activated thio group coupled to a suitable matrix by thiodisulfide exchange. This bond is reversible, and after removal by washing of the solubilizing agent the thiolcarrying antigen structure can be eluted by reduction of the disulphide bond by mercapto ethanol or dithiotrietol in the presence of solubilizing agent or glycoside.

Hydrophobic chromatography

This technique employs the interaction of an immobilized hydrophobic ligand of the octyl or phenyl type and hydrophobic surfaces of the antigen structure. Alternatively, this technique can be a method of bonding the solubilizing agent from the mixture to the ligand at the same time as the antigen structure can unadsorbed be recovered for continued treatment according to Example 4 (the dialysis method). Under other conditions the antigen structure can be bonded to the ligand, and as the solubilizing agent has no affinity for the ligand; one proceeds according to the dialysis method. Immobilization at high ion strength is effected by e.g. ammonium sulphate, and elution is effected at low ion strength with water or ethylene glycol.

Solubilizing of proteins or other immunogens with hydrophobic domains, purified or isolated with chromatographic methods is enhanced by supplementation of the solubilizing agent with lipid and/or polar organic solvents miscible in water and also by addition of sugars.

The complexes can thus contain membrane proteins from bacteria, it being then advantageous to first break the cell walls before the cell material is treated by the process above. Examples of bacteria from which hydrophobic proteins can be produced are e.g. Escherichia, Staphylococci, Haemaophilus, e.g. *H. influenzas*, Bordetella, e.g. *B. Pertussis*, Vibrio, e.g. *V. chlolerae*, Salmonella, e.g. *S. Typhi, S. paratyphi*, preferably adherence factor in Coli, e.g. pili K 88 and porin protein in e.g. Salmonella or outer membrane proteins from *B. pertussis* and *Neisseria meningitidis*.

Especially for bacteria, which contain comparatively little lipids and for which the lipoproteins and outer membrane proteins have strong hydrophobicity, the addition of lipids, sugars or polar organic solvents is suitable.

Examples of usable viruses with envelopes are Orthomyxoviridae such as influenza A,B,C, Paramyxoviridae, especially measles virus, mumps virus, parainfluenza 1,2,3 and 4.viruses, canine distemper virus and rinderpest virus, Rhabdoviridae, especially rabies virus, Retroviridae, especially feline leukemia virus and bovine leukemia virus, human immuno deficiency virus (HIV), Herpesviridae, especially Pseudorabies, Coronaviridae, Togaviridae, such as EEE,WEE,VEE (eastern, western and Venezuela equine encephalitis), yellow fever virus, especially bovine virus diarrhoea virus, and European swine fever virus Arenaviridae, Poxviridae, Bunyaviridae, Iridioviridae, especially African swine fever virus and among unclassified viruses, human hepatitis B-virus and Marburg/Ebola virus.

Examples of parasites which can be used according to the invention are Protoza, such as Toxoplasma, e.g. *Toxoplasma gondii*, Plasmodium, e.g. *Plasmodium vivax*, malarias, falciparium, *Teileria parvum ovale*, and Filaroidae, preferably Parafilaria aud Onchocerca, *Entamoeba histolytica*, anaplasma of various types, Schistosoma such as *Schistosoma haematobium*, mansoni, japonicum and Trypanosoma e.g. *Trypanosoma gambiense*, brusei or congolesi.

b) It is also possible to start from hydrophobic non-membrane proteins or from non-hydrophobic proteins or peptides. Non-hydrophobic proteins or peptides may be rendered hydrophobic by coupling hydrophobic groups to them or make non-accessible hydrophobic regions accessible by denaturation. Such proteins may derive from viruses with or without envelope, bacteria, mycoplasma, parasites. Examples of non-enveloped viruses with non-hydrophobic proteins are Picornaviridae (also considered to have hydrophobic proteins) e.g. foot-and-mouth disease virus, polio virus, Adenoviridae, Parvoviridae, e.g. feline parvo virus and swine parvovirus, Reoviridae, e.g. Rotavirus.

Examples of mycoplasma are *M. pneumonias*, mycoides, bovis, suis, hyorinos, orale, salivarium, hominis and fermentans.

These proteins or peptides can be obtained purified such as described under a) Purification and isolation.

The hydrophobic group that can be coupled to the non-hydrophobic proteins are straight, branched, saturated or unsaturateu uliphatic chains, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, or hydrophobic amino acids or peptides or other hydrophobic structures such as steroids. The length of the hydrophobic structure is adapted to the size and nature of the protein. As an example, it can be mentioned that a peptide with 10–15 amino acids (foot-and-mouth disease virus) suitably is brought out with two tyrosine at the amino or carboxy terminal end. A protein with a molecular weight of 70,000 daltons demands about 20 hydrophobic amino acids. Testing is made empirically. Thus, one uses especially peptides with 1 to 20 amino acids, preferably 1, 2, 3, 4, 5 amino acids, especially chosen among Trp, Ile, Phe, Pro, Tyr, Leu, Val, especially Tyr; cholesterol derivatives such as choline acid, ursodesoxycholine acid.

These hydrophobic groups must be bonded to a group that can be coupled to the non-hydrophobic protein such as carboxyl-, amino-, disulphide-, hydroxyl-, sulohydryl- and carbonyl group, such as aldehyde groups.

As hydrophobic groups that can be coupled are selected preferably carboxyl, aldehyde, amino, hydroxyl, and disulphide derivatives of methan, ethane, propane, butane, hexane, heptane, octane and peptides containing Cys, Asp, Glu, Lys, preferably octanal and Tyr.Tyr.-Tyr-Cys,-Asp or -Glu. The hydrophobic groups with a group that can be coupled must be dissolved in water with the aid of for example the solubilizing agents and detergents mentioned above or hydrochloric acid, acetic acid 67% by volume acetic acid, caustic liquor, ammonia, depending on what substance is to be dissolved. pH is then adjusted to the neutral direction without the substance precipitating; here it is to make sure that there is not obtained a pH value that denaturates the protein to which the hydrophobic group is to be coupled. Lipid may enhance the solubilization.

The hydrophobic molecule is added to the non-hydrophobic protein in the molar ratio of 10:1 to 0.1:1, preferably 1:1.

Hydrophobic groups with a carboxyl group as coupling molecule can be coupled to the protein through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of triethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrous acid can at a low temperature be converted to diazonium salts, which gives azo bonds with Tyr, His and Lys.

The hydroxyl groups with succinic anhydride can be converted to hemisuccinate derivatives which can be coupled as carboxyl groups.

Aldehyde groups can be reacted with amino groups in the protein to a Schiff's base.

Several coupling groups and methods are described in Journal of Immunological Methods, 59 (1983) 129–143, 289–299, Methods in Enzymology Vol 93 pp 280–33, and in Analytical Biochemistry 116, 402–407 (1981) which are here incorporated as references.

The proteins or peptides so produced having received hydrophobic groups are then complex-bonded with glycoside, as described in a), but here the purification steps for removing cell fragments can be omitted.

C) It is possible from hydrophilic proteins having enclosed hydrophobic domains to make them accessible by denaturing the protein. That is e.g. done with a low pH of about 2.5 or a high pH of about 9.5, by 3 M urea or at a high temperature, e.g. above 70° C. Examples of such proteins are immunoglobulins IgG, IgM, IgA etc. or other globular proteins, albumine, proteins from non-envelope viruses such as polio virus proteins, envelope proteins from virus which lost the hydrophobic region of the protein which often is the case with the envelope protein or retroviruses or the nucleoprotein of viruses. The immunoglobulin can e.g. be an antiidiotopic antibody. The proteins may be obtained as purified proteins described in b) and then complexbound to glycoside as described in c).

When starting from purified or synthetical proteins or peptides according to b) or c), they have a tendency to aggregate in the form of micelles during the preparation of iscoms. Therefore, the addition of one or more lipids, particularly cholesterol adds to the formation of the primary complex. Sometimes addition of a polar solvent e.g. ethanol is useful. The lipids are added to the protein or peptide as the solubilizing agents are added. The amount is not crucial. The molar ratio of lipid to protein or peptide should be at least 1:1. Then one of the four methods mentioned above can be used. When radioactive lipids are used, substantially no radio-activity can be detected in the primary immunogenic complex.

Hydrophilic peptides/polypeptides can be covalently coupled to fatty acids incorporated into liposomes consisting of e.g. cholesterol, phosphatidylcholine and the fatty acids in a ratio of 1:7:2. The peptide/polypeptide is extracted from the liposomes with a detergent and separated from excess lipid by centrifugation on a sucrose gradient (10–30% sucrose) containing detergent.

Iscoms can be made as above, preferably with the centrifugation or dialysis method. By use of the centrifugation method, Triton X-100 can be used for solubilization of the liposome complex. By the use of the dialysis method, the detergent can be dialyzed away (when for instance Octyl-glucoside is used).

The immunogenic complex prepared according to the invention can be used for specific immune-stimulation in humans and animals. They can thus be used for immunomodulation and diagnostics and as vaccines against diseases caused by bacteria, viruses, mycoplasmas and parasites and for producing antibodies, e.g. for research purposes.

Also mixtures of amphiphatic proteins from various bacteria or viruses can be added to produce vaccines against several afflictions.

The complexes may be used in human or veterinary compositions comprising iscom according to the invention possibly together with usual additives and fillers preferably in the form of a buffer solution of iscom, i.e. a TN-solution. They can also be used as analytical reagent and carrier for substances that one wants to increase the immunogenicity of.

The invention will be described in more detail with the following non-limiting examples.

EXAMPLE 1

By a mild denaturation at low pH hydrophobic regions of the bovine serum albumin (BSA 17) molecule is made accessible for formation of iscoms.

Two mg of BSA dissolved in 0.15 M citrate buffer pH 2.5 was incubated for 2 hrs with 2% N-dekanoyl-N-methyl-glucamin and an equimolar amount of lipid (cholesterol/phosphatidylcholine 1:1). The stock solution of lipid was 10 mg lipid/ml in distilled water with 20% N-dekanoyl-N-methyl-glucamin. Quil A was added to a concentration of 0.1%. The mixture was extensively dialysed against phosphate buffer pH 7.2 first for 6 hours at low temperature, then at $+4°$ C. for two days. Electron-microscopy confirmed that iscoms were formed.

To purify the preparation from material not bound to iscoms the preparation was centrifuged through 20% sucrose, on top of which 200 $\mu$l 10% sucrose with 0.1% Triton-X-100 was layered. A Kontron Tst 54 rotor was used a the centrifugation which was done for 10 hrs at 50,000 rpm at 20° C. The iscoms containing BSA were recovered from the bottom of the centrifuge tube by dissolving the pellet in 500 $\mu$l phosphate buffer pH 7.2. Between 5 to 10% of the BSA was recovered as iscoms.

The immunogenicity of the BSA-iscoms was tested in an immunization experiment in mice. A group of eight mice were immunized once with 1 $\mu$g of BSA in iscoms. Another group of five mice were immunized once with 0.1 $\mu$g of BSA-iscoms. Corresponding groups of eight mice were immunized with BSA not bound to iscoms. After a month the mice were bled and serum collected. The serum antibodies to BSA were measured in an ELISA. Eight mice immunized with 1 $\mu$g of i3COMS responded with a mean serum titre of 1/450 /range 1/100 to 1/1500, while mice immunized with 1 or 0.1.$\mu$g BSA not bound to iscoms did not respond to immunization with 1 or 0.1 $\mu$g of BSA. 3 of the mice immunized with 0.1 $\mu$g of BSA iscoms did not respond with low serum antibody titres to BSA, while two of the mice did.

EXAMPLE 2

A slight denaturation of BSA reveals hydrophobic regions of the molecule. That can be done at alcalic pH. To drive the reaction to the formation of iscoms an alcohol e.g. ethanol was included.

Two mg of BSA dissolved in 0.5 M carbonate buffer pH 9.6 containing 30% ethanol (ethylene glycol can also be used) were incubated for six hours. N-decanoyl-N-methyl-glucamin was added to a concentration of 2% together with equimolar amounts of lipid (cholesterol/phosphatidylcholine, see Example 1). Quil A was added to a concentration of 0.1%. The mixture was incubated for 30 to 60 minutes and then extensively dialyzed against phosphate buffer pH 7.2 first over night at room temperature then at 4° C. The iscoms were purified from non-iscom bound material by centrifugation as described in Example 1. Electron microscopy confirmed that iscom complexes were present. Furthermore these iscoms sedimented in a 10 to 50% sucrose gradient at the same rate as IgM, i.e. 19S. The recovery of BSA in iscoms was more than 50%.

EXAMPLE 3

Two mg of Glucagon were dissolved in carbonate buffer 5.5 M PH 9.6 containing 30% ethanol. This glucagon solution was treated in exactly the same way as bovine serum albumin (BSA) in Example 2. More than 50% of the glucagon was recovered in iscoms. That iscoms were formed was confirmed by electron microscopy and by determination of the sedimentation of the complexes in a 10 to 50% sucrose gradient using BSA (4S), thyroglobulin (19S) and IgM (19S) as standards.

EXAMPLE 4

Two mg angiotensin were dissolved in 0.5 M carbonate buffer pH 9.6 containing ethanol. This angiotensin solution was treated in the same way as bovine serum albumin (BSA) in Example 2. More than 50% of the angiotensin was recovered in iscoms. That iscoms were formed was confirmed by electron microscopy and by the determination of the sedimentation of the complexes in a 10 to 50% sucrose gradient using BSA (4S), thyroglobulin (19S) and IgM (19S).

EXAMPLE 5

The envelope protein gp 340 from the herpes virus Epstein Barr was reconstituted into iscoms.

200 μg of gp 340 dissolved in 0.15 M phosphate buffer pH 7,2 was incubated with 70 μg of lipid (cholesterol/phosphatidylcholine 1:1, see Example 1) and 2% N-dekanoyl-N-methyl-glucamin and incubated for 2 hrs at room temperature. Quil A was added to a concentration of 0.1%. The mixture was extensively dialyzed against phosphate buffer pH 7.2, first for 6 hrs at room temperature, then at +4° C. for 2 days. Electronmicroscopy confirmed that iscoms were formed. The gp 340 iscoms were purified from material not bound to iscoms by centrifugation through sucrose as described in Example 1.

EXAMPLE 6

Gp 340 iscoms have been prepared in different ways and below another variant is described.

300 ug of 9P 340 in 200 ul phosphate buffer pH 7.2 were added to a tube where 70 ug cholesterol were dried to the wall. Triton X-100 was added to a concentration of 2% and the mixture was kept for 2 hrs at room temperature. The mixture in a volume of 300 ul was layered on top of a gradient which from the top to the bottom consisted of 200 ul 15% sucrose with 1% Triton X-100 and 12 ml of 20 % sucrose in phosphate buffer as above containing 0.1% Quil A. The centrifugation was done at 40,000 rpm in a Beckman SW 40 rotor for 16 hrs and 20° C. The gradient was collected from the bottom in 500 ul portions and the gp 340 containing fractions were traced in an ELISA using a gp 340 rabbit antiserum. Electron microscopy was used to inform that iscoms were formed.

EXAMPLE 7

Gp 70 from Feline leukemia virus purified with immunosorbent technique from tissue culture fluid of F 422 cells was mildly denatured at low pH as described for bovine serum albumin (BSA) in Example 1. The same protocol as in Example 1 was also used to form gp 70 iscoms. That iscoms were formed was confirmed by electron microscopy. About 10% of the gp 70 was integrated into iscoms.

EXAMPLE 8

Gp 70 from Feline leukemia virus purified as described in Example 7 was slightly denatured as described for bovine serum albumin (BSA) in Example 2. The same protocol as in Example 2 was also used to form gp 70 iscoms at alcalic pH in the presence of ethanol. That iscoms were formed was confirmed by electron microscopy. More than 50% of gp 70 were integrated into iscoms.

EXAMPLE 9

Gp 120 of HIV purified from tissue culture fluid of HIV-infected H9-cells by immunosorbent technique was treated at low i)H as described for bovine serum albumin in Example 1. The same protocol was also used to form gp 120 iscoms. That iscoms were formed was confirmed by electron microscopy.

EXAMPLE 10

Gp 120 of HIV prepared from HIV infected H9 cells by immunosorbent technique was treated as described for bovine serum albumin (BSA) with alcalic pH and ethanol to reveal hydrophobic regions of the molecule. The same protocol as for BSA in Example 2 was used to form iscoms. That iscoms were formed was confirmed by electron microscopy.

EXAMPLE 11

A peptide representing the amino acid sequence 144-159 of VPl of Foot and Mouth Disease virus (FM.DV) was synthesized in five variants I. (Tyr$_3$) - FMD
II. N-palmitic acid - FMD
III. N-,capric acid - FMD
IV. N-capric acid - (FMD)$_2$
V. Lys-capric acid - FMD One mg of the peptide was mixed with an equimolar amount of lipid (cholesterol/phosohatidylcholine 1:1, see Example 1), N-decanoyl-N-methyl-glucamin at a concentration of 2% and Quil A at a final concentration of 0.1100. The mixture was incubated for 30 to 60 minutes at room temperature and dialyzed against phosphate buffer pH 7.2. The dialysis membrane had a cut off for a molecular weight of 1000. Electron microscopy revealed that iscoms were formed.

EXAMPLE 12

A peptide representing the amino acid sequence (palm)$_2$ Lys Glu Glu Asn Val Glu His Asp Ala of plasmodium falciparum antigen Pf 155 (Malaria) was synthesized with a palmitic acid conjugated to the N-terminal.

One mg of the peptide was mixed with an equimolar amount of lipid (cholesterol/phosphatidylcholine 1:1, see Example 1), N-decanoyl-N-methyl-glucamin at a concentration of 2% and Quil A at a final concentration of 0.1%. The mixture was incubated for 30 to 60 minutes at room temperature and dialyzed against phosphate buffer pH 7.2. The dialysis membrane had a cut off for a molecular weight cf 1000. Electron microscopy revealed the typical structure of iscoms.

EXAMPLE 13

A peptide representing the amino acid sequence Ala Glu Glu Asn Asp Glu Glu Asn Glu Glu Val Glu Glu Asn Val of plasmodium falciparum antigen Pf 155 (Malaria) was synthesized. Every third amino acid is hydrophobic and the structure of the peptide is a α-helix.

One mg of the peptide was mixed with an equimolar amount of lipid (cholesterol/phosphatidylcholine 1:1, see Example 1), N-decanoyl-N-methyl-glucamin at a concentration of 2% and Quil A at a final concentration of 0.1%. The mixture was incubated for 30 to 60 minutes at room temperature and dialyzed against phosphate buffer pH 7.2. The dialysis membrane had a cut off for a molecular weight of 1000. Electron microscopy revealed the typical structure of iscoms.

EXAMPLE 14

Two mg of the surface protein of Hepatitis B (HBs) introduced to yeast by recombinant DNA technique and produced by the yeast particle were solubilized with N-decanyl-N-methyl-glucamin at a concentration of 2%. An equimolar amount of lipid (cholesterol/phosphatidylcholine 1:1, see Example 1) and Quil A was added to a concentration of 0.1%. The mixture was incubated at room temperature for 2 hrs. After that the mixture was extensively dialyzed against phosphate buffer pH 7.2, for the first 4 to 6 hrs at room temperature, then at 4° C. Electron microscopy showed the typical formation of iscoms.

EXAMPLE 15

3 mg of bovine virus diarrhea virus (BVDV) dissolved in TN were solubilized by addition of Triton X-100 to a concentration of 1%. The solubilized virus was applied to a lectin column consisting of the lectin lens lentil immobilized to sepharose 4B (Parmacia, Uppsala). The column was equilibrated with TN* and after introduction of the virus material onto the column, it was washed with 5 column volumes TN containing 0.1% by volume Triton X-100 followed by 10 column volumes TN. Virus enveloped proteins were desadsorbed, by eluating buffer consisting of 0.2 M methyl-α-D-mannoside, 0.5% by weight of octyl-(β-D-glucoside dissolved in TN being added to columns. The fractions containing virus enveloped proteins were collected, Quila A was added to 0.1% by weight and 120 μg of lipid (cholesterol/phosphatidylcholine 1:1, see Example 1). The mixture was incubated for 30 to 60 minutes at room temperature and dialyzed against phosphate buffer pH 7.2. L6 (0.05 M Tris, 0.1 M NaCl, pH 7.2)

The example was repeated as above, but intralipid* was substituted for the lipid mixture described above. The formation of iscoms was confirmed by electron microscopy. L6 *Vitrum, Stockholm

EXAMPLE 16

3 mg of a smooth and a rough variant of porin protein from Brucella abortus strain 2308 were highly purified from contaminating proteins but with a contamination with LPS. The porin protein was kindly supplied by Dr. A.J. Winter, Department of Veterinary Microbiology, Cornell University, Ithaca, USA. The porin proteins were dissolved in one ml phosphate buffer, 20% sucrose an 350 μg lipid (cholesterol/phosphatidylcholine 1:1, see Example 1) over night at 4° C. Zwittergent was added to a concentration of 0.05%, N-decanoyl-N-methul-glucamin was added to a concentration of 0.5% and Quil A to a concentration of 0.1%. The mixture was extensively dialyzed against phosphate buffer pH 7.2 for two days, the fist 4 hrs at room temperature. The iscoms identified by electron microscopy were purified from non-iscom bound material by centrifugation as described in Example 1.

EXAMPLE 17

The nucleoprotein of cytomegalovirus a herpes virus—kindly supplied by Dr. B. Warren, National Institute of Health, Stockholm as a crude extract—was denatured at low pH as described in Example 1. Iscoms were prepared according to the protocol of Example 1. Electron microscopy revealed that iscoms were formed.

Balb/c mice were immunized twice (25 μg, 10 μg) with iscoms made from the malaria peptides described in Example 13 (A) and a mixture of the peptides described in Examples 12 and 13 (AB).

TABLE 2

| Immunogen (peptide) | titre after the 1$^{st}$ imm. | | titre after the 2$^{nd}$ imm. | |
|---|---|---|---|---|
| | peptide A | peptide B | peptide A | peptide B |
| A | 1:270 | 1:240 | 1:1380 | 1:400 |
| A | 1:300 | 1:220 | 1:1590 | 1:660 |
| A | 1:630 | 1:480 | 1:2100 | 1:800 |
| AB | 1:410 | 1:250 | 1:2089 | 1:500 |

EXAMPLE 18

A mixture of the glycoprotein and the nucleoprotein of cytomegalovirus was kindly supplied by Dr. B. Wahren, National Institute of Health, Stockholm as a crude extract. This glycoprotein-nucleoprotein preparation was treated at low pH and iscoms were prepared as described in Example 1. Electron microscopy revealed that iscoms were formed. In Table I it is shown that monkeys immunized with the cytomegalovirus iscoms induced high cellmediated immunity. For a prospective vaccine against cytomegalovirus it is important that cellmediated immunity is elicited.

TABLE 1

Proliferative reactivity of peripheral blood cells from CMV-immunized monkeys to CMV antigen in solid phase

| Monkey no. | Dose | Immunizing CMV antigen Given with | Net cpm$^2$ ± SD Lympho-cytes | Mono-cytes | CMV$^b$ | IgG titer PHA |
|---|---|---|---|---|---|---|
| 1 | low | — | 499 ± 229 | 800 ± 1044 | 200 | 160 |
|   | high | — | <100 | <100 | 500 | 6400 |
| 2 | low | — | <100 | <100 | 300 | 400 |
|   | high | — | 700 ± 519 | <100 | 400 | 24000 |
|   | high | monocytes | 3800 ± 1700 | n.d. | 13000 | 30000 |
| 3 | low | — | 854 ± 250 | <100 | 300 | 500 |
|   | high | — | <100 | <100 | 3200 | 24000 |
|   | high | monocytes | 2800 ± 240 | n.d. | 22000 | 18000 |
| 4 | low | monocytes | 423 ± 166 | 441 ± 317 | 2000 | 400 |
|   | high | monocytes | 3516 ± 3202 | 106 + 160 | 10000 | 18000 |
| 5 | low | monocytes | 866 ± 709 | 833 ± 288 | 10000 | 100 |
|   | high | monocytes | 30200 ± 5300 | 660 ± 280 | 27000 | 22000 |
| 6 | low | monocites | <100 | 490 ± 440 | 6000 | 160 |
|   | high | monocytes | 27000 ± 21000 | <100 | 52000 | 25000 |
| 7 | low | iscoms | 36400 ± 6500 | n.d. | 32700 | 2100 |
| 8 | low | iscoms | 49500 ± 9000 | n.d. | 15300 | 15000 |
| Human control, CMV seropositive | | | 37300 ± 6500 | 2600 ± 513 | 45000 | 12000 |
| Human Control, CMV seronegative | | | <100 | <100 | 50000 | 100 |

$^2$Before immunization, all animals had net cpm 1000 with lymphocytes and CMV antigen (546 ± 58 cpm with CMV, net cpm 100); monocytes and CMV (322 ± 208 cpm,, net cpm 100) or lymphocytes and monocytes with CMV (709 ± 425 cpm with CMV, net cpm 211 ± 300)
$^b$Before immunization, all animals had CMV IgG titers 100, except monkey no. 8, which was preimmunized with CMV nuvleocapsid antigen.

EXAMPLE 19

300 μg of gp 340, an envelop protein from Epstein Barr virus (a herpes virus) in 200 ul PBS, is added to a tube where 70 μg of chloesterol is dried to the wall. Triton X-100 is added and the mixture is kept at room temperature for 2 hrs. The mixture in a volume of 300 μl is layered on top of a gradient, which from the top to the bottom consists of 200 μl 15% sucrose with 1% TX-100 and 12 ml of 20% sucrose in PBS containing 0.1% Quil A. The centriguation was done at 40,000 rpm in a Beckman SW rotor for 16 hrs and 20° C. The gradient was collected from the bottom in 500 μl portions. The gap 340 mixed with detergent and cholesterol can be reconstituted into iscoms by the dialysis method. In that case Quil A was added to a final concentration of 0.1% before dialysis. It is then preferable to have a detergent which easily can be dialyzed away, e.g. octyl-clycoside which was used in this case.

The mixture was then dialyzed for 48 hrs at 4°-60° C. against PBS (also TN buffer has been used). The formation of iscoms was verified in electron microscopy. The advantage of using e.g. envelope proteins of different virus purified with different methods, i.e. the method of choice is obvious.

EXAMPLE 20

Three sequences hybride DNA product from FELV gp 70 were conjugated to stearyl amine incorporated into liposomes with the glutaraldehyde two-step method. 10 mg (10 mg/ml) liposomes in PBS pH 7 were activated with a final concentration of 1,25% glutardialdehyde at room temperature over night. Excess glutardialdehyde was removed by either dialysis or gel filtration.

3 mg activated liposomes were mixed with 1 mg of each FELV gp 70 polypeptide, the volume was adjusted to 1 ml and the pH was raised by adding 100 μl M NACO pH 9.6. The mixture was incubated over night, and purified from unbound polypeptide by gel filtration (e.g. S-300).

The polypeptide-fatty acid was extracted with 2% N-decanoyl-N-methylglucamine (MEGA-10) and separated from excess lipid by centrifugation on a sucrose gradient (5-30% sucrose) containing 0.3% MEGA-10.

The polypeptide was collected, Quil A was added to a final concentration of 1% and the mixture was extensively dialyzed against PBS, the first 4-6 hrs at room temperature, then at +40° C.

EXAMPLE 21

3 mg bovine IgG in 0.5 M carbonate buffer pH 0.6 containing 30% ethanol were incubated for six hours. N-decanyl-N-methyl-glucamin was added to a concentration of 2% together with equimolar amounts of lipid (cholesterol/phosphatidyicholine 1:1, see Example 1). Quil A was added to a concentration of 0.1%. The mixture was incubated for 30 to 60 minutes and then extensively dialyzed against phosphate buffer pH 7.2 first over night at room temperature, then at 4° CA. The iscoms were purified from non-iscom bound material by centrifugation as described in Example 1. Electron microscopy confirmed that iscoms were present. Furthermore these iscoms sedimented in a 10 to 50% sucrose gradient at the same rate as IgM, i.e. 19S.

EXAMPLE 22

Two peptides representing aminoacid sequences of plasmodium falciparum antigen Pf 155 (Malaria) (described in Examples 12 and 13) were synthesized. Each peptide was used to form peptide/protein iscoms. 7-quimolar amounts of peptide, membrane protein and lipid (cholesterol/phosphatidyl choline 1:1, see Example 1) were mixed with N-decanyl-N-methyl-glucamin and Quil A to a final concentration of 2% and 0.1% respectively. The mixture was incubated for 30-60 minutes at room temperature and dialyzed against phosphate buffer pH 7.2. The dialysis membrane had a molecular weight cut off of 1000 Kd. Electron microscopy revealed the typical structure of iscoms.

I claim:

1. In a method for producing an immunogenic complex between an antigen and a polar triterpensaponin having hydrophobic regions, comprising the steps of
   a. solubilizing the antigen with a solubilizing agent to form a complex between the solubilizing agent and the antigen,
   b. contacting the solubilized antigen with a solution containing a polar triterpensaponin having hydrophobic regions present at a concentration of at least the critical micellar concentration to form a protein-triterpensaponin complex either
      i. by separating the antigen from the solubilizing agent and immediately transferring the separated antigen to the glycoside containing solution, or
      ii. by removing the solubilizing agent after contact has been made with the glycoside containing solution, and
   c. isolating and purifying the protein-glycoside complex which results from said contact, wherein the antigen has exposed hydrophobic peptide domains through which the hydrophobic regions of the glycoside bind, said domains being derived from
   i. amphiphatic proteins or peptides which have hydrophobic domains accessible without modification,
   ii. hydrophilic proteins or peptides made amphiphatic through covalent attachment of hydrophobic groups, or
   iii. amphiphatic proteins or peptides having hydrophobic domains being made accessible through chemical means or by heat treatment, wherein the solubilizing agent is selected from the group consisting of non-ionic detergents, ionic detergents, Zwitterionic detergents, or detergents based upon gallic acid, and wherein the resulting complex has
   i. a lower sedimentation constant that the corresponding micelles
   ii. a higher sedimentation constant that the corresponding monomeric form of the antigen, and
   iii. an open spherical structure, the improvement comprising adding to the solubilized antigen at least one lipid selected from the group consisting of fats, glycerol ethers, waxes, phospholipids, glycolipids, isoprenoids, steroids, and mixtures thereof, in a molar ratio of lipid to antigen of between 0.1:1 to 100:1, prior to contact of the solubilized antigen with the glycoside-containing solution in step b.i. or b.ii.

2. A process according to claim 1, characterized in that the lipids are miscible in the solubilizing agent.

3. A process according to claim 1, characterized in that said at least one lipid comprises a steroid.

4. A process according to claim 1, wherein the antigen is selected from the group consisting of
   (a) amphiphatic proteins or peptides with hydrophilic and hydrophobic groups derived from or being membrane proteins or membrane peptides from enveloped viruses, bacterias, mycoplasmas, parasites or animal cells, or such proteins or peptides produced by hybrid DNA technique, or molecules produced synthetically.
   (b) hydrophilic proteins or peptides made amphiphatic by hydrophobic groups coupled to them, which proteins or peptides derive from viruses, bacterias, mycoplasmas, parasites, whole cells or are synthesized or obtained by hybrid DNA technique, and
   (c) amphiphatic proteins or peptides obtained by inaccessible hydrophobic parts of hydrophilic proteins made accessible by chemical means, which proteins derive from the microorganisms or cells mentioned above or are obtained by hybrid DNA technique, or are synthesized.

5. In a method for producing an immunogenic complex between an antigen and a polar triterpensaponin having hydrophobic regions, comprising the steps of
   a. solubilizing the antigen with a solubilizing agent to form a complex between the solubilizing agent and the antigen,
   b. contacting the solubilized antigen with a solution containing a polar triterpensaponin having hydrophobic regions present at a concentration of at lest the critical micellar concentration to form a protein-teterpensaponin complex either
      i. by separating the antigen from the solubilizing agent and immediately transferring the separated antigen to the glycoside containing solution, or
      ii. by removing the solubilizing agent after contact has been made with the glycoside containing solution, and
   c. isolating and purifying the protein-glycoside complex which results from said contact, wherein the antigen has exposed hydrophobic peptide domains through which the hydrophobic regions of the glycoside bind, said domains being derived from
   i. amphiphatic proteins or peptides which have hydrophobic domains accessible without modification,
   ii. hydrophilic proteins or peptides made amphiphatic through covalent attachment of hydrophobic groups, or
   iii. amphiphatic proteins or peptides having hydrophobic domains being made accessible through chemical means or by heat treatment, wherein the solubilizing agent is selected from the group consisting of non-ionic detergents, ionic detergents, Zwitterionic detergents, or detergents based upon gallic acid, and wherein the resulting complex has
   i. a lower sedimentation constant than the corresponding micelles
   ii. a higher sedimentation constant than the corresponding monomeric form of the antigen, and
   iii. an open spherical structure, the improvement comprising adding to the solubilized antigen at lest one lipid selected from the group consisting of sterols, phosspholipids, fatty acids and mixtures thereof, in a molar ratio of lipid to antigen of between 0.1:1 to 100:1, prior to contact of the solubilized antigen with the glycoside-containing solution in step b.i. or b.ii.

6. A method for preparing immunogenic complexes, comprising
   a) combining an immunogenicaly effective amount of an amphipathic antigenic protein or peptide with a lipid component, a detergent, and a glycoside, said lipid component comprising at least one lipid selected from the group consisting of sterol and phospholipid, whereby a protein complex is formed, said glycoside having both hydrophobic and hydrophilic regions and being present in at least the critical micelleforming concentration, and said glycoside and said lipid component being present in relative amounts effective to produce an immunogenic complex; and
   b) removing the detergent from the resulting protein complex.

7. The method according to claim 6, wherein the lipid component consists essentially of a sterol which is free of phospholipid.

8. The method according to claim 7, wherein the sterol is cholesterol.

9. The method according to claim 6, wherein the glycoside is a saponin.

10. The process of claim 9, in which the saponin is a saponin from Quillaja saponaria Molia, Aesculus hippocastanum or Glypsophilia struthium.

11. The process of claim 10, in which the spaonin is DQ, Quil A, aescine or sapoalbin.

12. The process of claim 11, in which the saponin is Quil A.

13. The process of claim 6, in which the detergent used is a non-ionic, ionic or zwitter-ionic detergent or a cholic acid based detergent.

14. The process of claim 13, in which the detergent is octylglucoside.

15. The process of claim 13, in which the detergent is an alkylphenylpolyosyethylene ether.

16. The process of claim 15, in which the detergent is Triton X-100 ®.

17. The process of claim 6, in which the removal of the detergent from the protein complex is carried out by centrifugation in a density gradient, by dialysis or by chromatography.

18. Pharmaceutical composition comprising an immunogenic complex obtained by means of the process of claim 9.

19. A method for preparing immunogenic complexes, comprising
  a) combining an immunogenicaly effective amount of an amphipathic antigenic protein or peptide with a lipid component, a detergent, and a glycoside, said lipid component consisting essentially of at least one lipid selected from the group consisting of sterol and phospholipid, whereby a protein complex is formed, said glycoside having both hydrophobic and hydrophilic regions and being present in at least the critical micelle-forming concentration, and said glycoside and said lipid component being present in relative amounts effective to produce an immunogenic complex; and
  b) removing the detergent from the resulting protein complex.

* * * * *